(12) United States Patent
Guo et al.

(10) Patent No.: US 12,158,423 B2
(45) Date of Patent: Dec. 3, 2024

(54) OPEN CHAMBER ACOUSTIC DEVICE TO MEASURE CELL BINDING FORCE

(71) Applicant: The Trustees of Indiana University, Indianapolis, IN (US)

(72) Inventors: Feng Guo, Bloomington, IN (US); Zheng Ao, Bloomington, IN (US); Hongwei Cai, Bloomington, IN (US)

(73) Assignee: The Trustees of Indiana University

( * ) Notice: Subject to any disclaimer, the term of this patent is extended or adjusted under 35 U.S.C. 154(b) by 920 days.

(21) Appl. No.: 17/107,278

(22) Filed: Nov. 30, 2020

(65) Prior Publication Data

US 2021/0364439 A1     Nov. 25, 2021

Related U.S. Application Data

(60) Provisional application No. 63/027,076, filed on May 19, 2020.

(51) Int. Cl.
 *C12M 1/34*    (2006.01)
 *B01L 3/00*    (2006.01)
 (Continued)

(52) U.S. Cl.
 CPC ..... *G01N 21/6458* (2013.01); *G01N 21/6428* (2013.01); *G01N 33/4833* (2013.01);
 (Continued)

(58) Field of Classification Search
 None
 See application file for complete search history.

(56) References Cited

U.S. PATENT DOCUMENTS 10,444,179 B2 * 10/2019 Paik ................. G01N 33/54353
2016/0313316 A1 * 10/2016 Yao .................. G01N 33/54366
(Continued)

OTHER PUBLICATIONS

Dultsev et al. "Hearing" Bond Breakage. Measurement of bond rupture forces using a quartz crystal microbalance, Langmuir 2000, vol. 16, pp. 5036-5040 (Year: 2000).*
(Continued)

*Primary Examiner* — Neil N Turk
(74) *Attorney, Agent, or Firm* — Faegre Drinker Biddle & Reath

(57) ABSTRACT

Disclosed is an apparatus, such as an acoustic for parallel profiling cell-matrix adhesion at single-cell level via the introduction of localized and uniform acoustic streaming into an open chamber microfluidic device. The adherent cells within the open chamber can be detached by the streaming-induced Stokes drag force, thereby allowing an accurate determination of the relevant forces and kinetics. The current device and method includes the digital regulation of acoustic streaming from a low level to high levels, and a large number of adherent cells can be ruptured from the substrate, and the particular adhesive forces and kinetics can be determined by the applied power. The acoustic device and the associated detachment technique can characterize the adhesion dynamics and kinetics of cells, such as mammalian cells and bacterial cells. And because fibronectin mimics cells and/or cell matrices, the acoustic device and the corresponding method has broad application in determining the force(s) required to detach cells from other types of cells and/or cell matrices.

8 Claims, 13 Drawing Sheets

(51) Int. Cl.
*C12M 1/00* (2006.01)
*G01N 15/1429* (2024.01)
*G01N 15/1433* (2024.01)
*G01N 21/64* (2006.01)
*G01N 29/00* (2006.01)
*G01N 33/483* (2006.01)

(52) U.S. Cl.
CPC . *G01N 2021/6439* (2013.01); *G01N 2201/02* (2013.01); *G01N 2201/12* (2013.01)

(56) References Cited

U.S. PATENT DOCUMENTS

2019/0255527 A1* 8/2019 Candelli ............ G01N 15/1429
2019/0317050 A1* 10/2019 Zhou ........................ C12N 5/06

OTHER PUBLICATIONS

Saitakis et al. Acoustic sensors as a biophysical tool for probing cell attachment and cell/surface interactions, Cellular and Molecular Life Sciences, 2012, vol. 69, pp. 357-371 (Year: 2011).*

* cited by examiner

OPEN CHAMBER ACOUSTIC DEVICE TO MEASURE CELL BINDING FORCE

CROSS-REFERENCE TO RELATED APPLICATION

The present application claims the benefit of and priority to U.S. Provisional Application No. 63/027,076, filed on May 19, 2020, the entire contents of which being hereby expressly incorporated herein by reference.

FIELD OF THE DISCLOSURE

The devices and methods described herein generally relate to a device, such as an acoustic device, for profiling cell adhesion strength and kinetics utilizing acoustic streaming.

BACKGROUND

The investigation of cell-matrix adhesion is an important aspect for biomedical research and translational medicine. Mammalian cells rely on their bonds to tissue extracellular matrix (ECM) to obtain structural support. The cell-matrix interaction also plays an essential role in regulating key cellular functions, including cell migration, differentiation, proliferation, and gene expression. Thus, cell-matrix adhesion not only impacts tissue development and orogenesis, but cell-matrix adhesion also impacts pathological processes, such as inflammation, tumor growth, and cancer metastasis. The ability to the measure cell-matrix adhesion and/or the cell binding affinity of similar and dissimilar cells, such as various types and/or combinations of mammalian cells, immune cells, cancer cells, nerve cells, bacterial cells, to other cells and/or cell matrices for detecting and monitoring diseases, detecting and monitoring cell receptor affinity, detecting and monitoring immunological response(s) and performing drug screening, is an important research and diagnostic tool.

As an example of cancer detection, among the pathological processes, cancer metastasis remains the greatest challenge in the clinical management of cancer, accounting for the majority of cancer-related mortality. During cancer metastasis, circulating tumor cells (CTCs) released from primary tumors intravasate the vasculature of normal tissue, which allows CTCs to establish themselves at distant locations and form metastases. Adhesion of CTCs to the endothelium ECM is a key step for tumor metastasis colonization. Moreover, the number of CTCs far exceeds the number of overt metastatic lesions that develop. Adequate models and methods have impeded investigation of the molecular and cellular events during metastatic colonization. Therefore, exploring the adhesive interactions between CTCs and the ECM potentially leads to the development of novel diagnostics, as well as novel targets, to treat or prevent metastasis.

There are existing approaches that have been and are used to profile the interaction of cells and substrates, particularly cell adhesion kinetics and strength, such as cell-matrix adhesion forces. These existing approaches may include various technologies, such as atomic force microscopy (AFM), surface plasmon resonance (SPR) technology, fluid-flow devices, microfluidics, shear-spinning disks, centrifugation methods, and micropipette aspiration. The profiling of cell adhesion kinetics and strength requires both accurate single-cell level measurements and measurements of a large-number datasets to capture rare cell events and to account for the heterogeneity in cell behavior of cell subsets.

Regarding AFM, a single living cell is typically immobilized at the cantilever tip of an AFM device, and it is used as a measuring probe to measure the force and kinetics of cell detachment by setting this single cell in contact with the matrix surfaces for a defined period of time. Micropipette aspiration has been widely used to directly quantify cell-substrate adhesion force by applying a constant-rate aspiration pressure to rupture a single adhered cell from the matrix. SPR technology is particularly suitable for real-time and label-free investigation of cell-substrate interactions by measuring the local refractive index distribution. These three methods are very sensitive and capable of providing real-time and high spatial resolution information on cell-substrate interaction at the single-cell level, but are limited in measuring a large number of cells substantially simultaneously or in parallel. That is, these methods are incapable of measuring large populations of cells. Moreover, AFM and micropipette aspiration devices require physical contact with cells.

Fluid-flow devices, shear-spinning disks and centrifugation methods may enable measurements of large cell populations through the use of shear force induced by hydrodynamic flow or centrifugation to detach adherent cells from the substrate by adjusting the applied forces. However, shear-spinning disks and centrifugation methods lack the ability to capture real-time images of the cells and accurately measure the rupture force between cells or between the cell(s) and the substrate. Despite these methods that enable measurements of large cell populations, they may not access the accurate measurement of rupture forces because of the lack of real-time imaging and precise force control with bulk setups and normally require a relatively large number of cells (e.g., tens of thousands to several millions).

These cell-matrix adhesion measurements are still not suitable for the measurement of various cells and cell types, including but not limited to CTCs, because they cannot simultaneously provide a high-precision measurement for a relatively low number of cells (several tens to several hundreds) within a short time period (e.g., several tens of minutes to an hour).

Current microfluidic devices may have the potential for parallel profiling cell-matrix adhesion force at the single-cell level. By tuning hydrodynamic flows in a microchannel, the cultured cells within the closed chamber can be detached by the hydrodynamic shear force under different conditions, and the cell detachment process can be captured simultaneously using a time-lapse microscope. However, current hydrodynamic-flow-based microfluidic methods are not ready for wide applications in basic biomedical research such as single cell-matrix adhesion studies for a few reasons. Firstly, current hydrodynamic-flow-based microfluidic methods do not provide an accurate measurement of cell detachment because it is difficult to quickly and stably adjust the flow rate in the microfluidic channel. That is, it may take an undesirable amount of time to increase a low flow rate to a high flow rate, and if the time to increase the flow rate is increased, a variable flow rate in the microfluidic channel is created and an undesirable varying shear force is induced, thereby preventing the precise determination of the amount of force causing the detachment of single cells from a substrate. Secondly, the continuous (or slowly varying) hydrodynamic flow in the microfluidic channel provides not only a shear force for adherent cells but also a continuous (or changing) compress stress force for these cells, which limits the maximal shear force produced by this technique for cell detachment measurement. Thus, for exploration of the cell-matrix interaction, there are still unmet needs for improving hydrodynamic-flow-based microfluidics.

SUMMARY

What is needed is a device and method for accurately profiling and monitoring cell adhesion kinetics and strength metrics for both single-cell level measurements and measurements of a large-number datasets so as to capture rare cell events and to account for the heterogeneity in cell behavior of cell subsets while precisely controlling and determining the force applied to the cells in real-time. The acoustic device of the present disclosure provides for parallel profiling cell-matrix adhesion at single-cell level via the introduction of localized and uniform acoustic streaming into an open chamber microfluidic device because the adherent cells within the open chamber can be detached by the streaming-induced Stokes drag force, thereby allowing an accurate determination of the relevant forces and kinetics. For example, using an open chamber versus a closed chamber increases the ease of use of the acoustic device and increases the rate at which the cells can be tested, which, in turn, increases the device's overall throughput of cells. Additionally, the current device and method includes the digital regulation of pulsed acoustic power from a low level to high levels, and hundreds of adherent cells can be ruptured from the substrate, and the particular adhesive forces and kinetics can be determined by the applied power.

By digitally tuning the input amplitude, the acoustic streaming force can be accurately adjusted and set to create very low forces, such as in the range of hundreds of piconewtons (pN) to tens of nanonewtons (nN), thereby producing an accurate continuous constant or variable flow of liquid which in turn induces a corresponding constant or variable shear force so that the force for the detaching single cells from a substrate can be precisely assessed and determined. The present disclosure demonstrates that the acoustic device and the associated detachment technique can characterize the adhesion dynamics and kinetics of cells, such as cancer cells, to fibronectin. And because fibronectin mimics cells and/or cell matrices, the acoustic device and the corresponding method has broad application in determining the force(s) required to detach cells from other types of cells and/or cell matrices. That is, the acoustic device and the corresponding method can be used to determine substantially simultaneously or in parallel the force(s) required to detach cell-to-cell binding or cell-to-matrix binding for cells and/or cell matrices disposed within a plurality of open chambers within an acoustic device.

The acoustic device and corresponding method cannot only be used to measure the cell binding affinity of similar and dissimilar cells, such as mammalian cells, immune cells, cancer cells, nerve cells, bacterial cells, to other cells and/or cell matrices for detecting and monitoring diseases, but the acoustic device and corresponding method can also be used to screen new markers, drugs and/or new therapies by measuring the force(s) required to detach the markers or new therapies from cells and/or cell matrices. For example, the acoustic device and the corresponding method can be used to test the adhesion or rupture force of the markers or new therapies from cells and/or cell matrices. Additionally, the acoustic device and the corresponding method can be used to testing cell-matrix interaction for development materials, implantable devices, tissue, bones and/or organs. For example, the acoustic device and the corresponding method can be used to test the adhesion or rupture force of materials and devices relative tissue, bones and/or organs s. In short, the acoustic device and hydrodynamic-flow-based microfluidic method offers multiple advantages over previous conventional approaches such as high-throughput performance, a wide range of detachment force, low sample consumption, and compatibility with a real-time imaging system and other modules. As such, the acoustic device of the present disclosure may also be referred to as an acoustofluidic device.

A system for determining a cell binding force of the present disclosure comprises: an acoustic device comprising: a substrate; a plurality of open chambers disposed on the substrate, wherein the plurality of open chambers are configured to retain a suspension fluid comprising a plurality of cell matrices; one or more acoustic generators disposed in the plurality of open chambers, wherein the one or more acoustic generators are configured to create surface acoustic waves or bulk acoustic waves within the open chamber and produce a stream of the suspension liquid contained within the open chamber; an imaging device configured to image the plurality of cell matrices in the plurality of open chambers; a signal generator electrically coupled to the one or more acoustic generators, wherein the signal generator produces a signal having an amplitude; a controller comprising one or more processors and non-transitory computer readable medium storing instructions for execution by the one or more processors, wherein execution of the instructions by the one or more processors cause the one or more processors to: increase the amplitude of the signal; image the plurality of cell matrices and identify the amplitude of the alternating signal when one or more cells detach from one of the plurality of cell matrices; determine an estimated velocity of the stream of the suspension liquid based on the amplitude of the signal, wherein the estimated velocity is determined via model comprising a three-dimensional pattern of acoustic streaming; and calculate a force at which one or more cells detach from one of the plurality of cell matrices using the estimated velocity.

The system of the previous paragraph, wherein each of the one or more acoustic generators disposed in the plurality of open chambers comprises an interdigital transducer.

The system of any of the previous paragraphs, wherein the interdigital transducer is a focused interdigital transducer.

The system of any of the previous paragraphs, wherein the focused interdigital transducer comprises a plurality of electrodes.

The system of any of the previous paragraphs, wherein the plurality of electrodes are arched shaped.

The system of any of the previous paragraphs, wherein the open chamber comprises a circular shaped wall having a center.

The system of any of the previous paragraphs, wherein one of the acoustic generators disposed in the plurality of open chambers comprises a plurality of electrodes disposed between the circular shaped wall and the center.

The system of any of the previous paragraphs, wherein the plurality of electrodes are arched shaped.

The system of any of the previous paragraphs, wherein the plurality of electrodes have a focusing angle of between about thirty degrees and seventy-five degrees.

The system of any of the previous paragraphs, wherein the plurality of electrodes have a focusing angle of between about forty degrees and seventy degrees.

The system of any of the previous paragraphs, wherein the plurality of electrodes have a focusing angle of between about forty five degrees and sixty five degrees.

Another system for determining a cell binding force comprises: an acoustic device comprising: a substrate; a plurality of open chambers disposed on the substrate, wherein the plurality of open chambers are configured to retain a suspension fluid comprising two or more cells bound to one another; one or more acoustic generators disposed adjacent the plurality of open chambers, wherein the one or more acoustic generators are configured to create an acoustic stream within the open chamber; an imaging device configured to substantially simultaneously or in parallel image the two or more cells in each of the plurality of open chambers; a signal generator electrically coupled to the one or more acoustic generators, wherein the signal generator produces a signal having an amplitude; a controller comprising one or more processors and non-transitory computer readable medium storing instructions for execution by the one or more processors, wherein execution of the instructions by the one or more processors cause the one or more processors to substantially simultaneously or in parallel: digitally increase the amplitude of the signal to one or more acoustic generators; image the two or more cells in each of the plurality of open chambers and identify the amplitude of the alternating signal for each of the plurality of open chambers when one of the two or more cells detach from an other of the two or more cells; determine an estimated velocity of the stream of the suspension liquid in each of the plurality of open chambers based on the amplitude of the signal; and calculate a force at which one or more cells detach from the other of the two or more cells in each of the plurality of open chambers using the estimated velocity.

The system of the previous paragraph, wherein the one or more acoustic generators produces acoustic surface waves.

A method of determining a cell binding force of the present disclosure comprises: providing an acoustic device comprising: an open chamber; an acoustic generator disposed in the open chamber, wherein the open chamber is configured to retain a suspension fluid comprising a plurality of cell matrices; applying an alternating signal to the acoustic generator at an amplitude, thereby creating surface acoustic waves or bulk acoustic waves within the open chamber and producing a stream in the suspension liquid contained within the open chamber; increasing the amplitude of the alternating signal; imaging the plurality of cell matrices while the amplitude of the alternating signal is increasing; determining, via imaging, when one or more cells detach from one of the plurality of cell matrices; identifying the amplitude of the alternating signal when the one or more cells detach from one of the plurality of cell matrices; determining an estimated velocity of the stream of the suspension liquid based on the amplitude of the alternating signal, wherein the estimated velocity is determined via model comprising a three-dimensional pattern of acoustic streaming; and calculating a force at which the one or more cells detach from one of the plurality of cell matrices using the estimated velocity.

The method of the previous paragraph, wherein the stream in the suspension liquid is created by two vortexes in the suspension fluid.

The method of any of the previous paragraphs, wherein the stream is disposed between the two vortexes in the suspension fluid.

The method of any of the previous paragraphs, the estimated velocity of the stream of the suspension liquid is based at least in part of an area of the stream disposed between the two vortexes.

As discussed above, the acoustic device and the corresponding method can be used to manipulate and/or investigate the various types of cells and cellular bodies, including the adhesion force or detachment force for the various types of cells and cellular bodies. The cellular bodies may be cell portions like subcellular organelles, cell nuclei, and/or mitochondria. However, the cellular bodies may also be unicellular or pluricellular, such as small clumped cell groups, plant or animal biopsy, dividing cells, budding yeast cells, colonial protists, etc. The cellular bodies may also be animal embryos in an early stage of development (e.g. the morula-stadium of a mammal, possibly a human embryo). In particular cases different types of cellular bodies may be studied together, such as cellular bodies from a mucosal swab, blood sample, or other probing techniques.

The acoustic device and the corresponding method enables parallel studies on various properties of the one or more cellular bodies. Particular examples are presence, absence and/or quantification of abundance of biomolecules on the cellular bodies, surface adhesion forces and/or adhesion kinetics of the cellular bodies, to the functionalized surface portion, differences in any of the above under influence of biological processes active in the cellular bodies. The presently provided acoustic device and method enables studies on the various properties of multiple individual cellular bodies in parallel, since multiple cellular bodies in the sample may contact and interact with the functionalized wall surface portion. This may increase accuracy of the study results and false positives or false negatives may be avoided.

The presently provided acoustic device and method enables studies on cellular bodies per se, without adhesion of foreign objects to the cellular bodies such as microbeads, magnets, chromophores, antibodies, various other labels etc. which is generally required in present-day cell manipulation and -study techniques. The cellular bodies may remain essentially unharmed by the present method and it is envisioned that after performing the method, the cellular bodies could be administered to a test subject and/or returned to a subject having donated the cellular bodies for studying; e.g. one or more of T-cells, leukocytes, erythrocytes and similar cellular bodies may be withdrawn from a subject, be studied in accordance with the method, and could thereafter be further analyzed with various other methods (single-cell sequencing, fluorescence microscopy, cryo-electron microscopy, etc.) and/or administered to another subject (e.g. blood donation) or returned to the original subject itself. Smaller cellular bodies, e.g. taken from blood plasma, may also be studied prior to donation or return. Similarly, spermatozoa and/or eggs could be studied before artificial in-utero or in-vitro fertilization, and fertilized eggs and/or first-stage embryos (e.g. morula or blastula stage) may be screened before implantation in a female subject for gestation.

Suitable interaction moieties may comprise an antibody for selective binding to a particular target, e.g. a microbial cell or a cancer cell, specific antibodies exist for several major hospital infections. Such interaction moiety may normally be effective to deliver a conjugate of the interaction moiety to a predetermined pathological site in a mammal. A pathological site may comprise a target moiety which, together with the interaction moiety, constitutes a specific binding pair. In the present case, the interaction moiety may be attached to the wall in the functionalized wall portion, e.g. by direct attachment or by forming the interaction moiety from or with a primer, and a binding pair may have sufficient binding force to adhere the cellular body to the functionalized wall portion.

The interaction moiety may comprise an antibody, or an antibody fragment that binds to a cell-surface antigen, or a ligand or ligand fragment that binds specifically to a cell surface receptor. From this group anti bodies, or antibody fragments, that bind to a cell-surface antigen may be preferred because of their binding selectivity. For instance, cancer cells usually have tumor associated antigens on their surface. Their complementary antibodies will bind very selectively to these tumor associated antigens. Ligand or ligand fragments however are also suitable. Various peptides are known to bind their cognate receptors with high affinity and thus would be suitable ligands for conjugation to the radioisotopes of the invention. Receptors are plasma membrane proteins which bind molecules, such as growth factors, hormones and neurotransmitters. Tumors develop from particular cell types which express certain subsets of these receptors. Taking advantage of this binding affinity between receptor and ligand enables target-specific studies and/or identification of cellular bodies.

Immune response relies on a complex interaction cascade between immune cells and their cell surfaces. For instance, B-cell activation depends on the binding of the B-cell receptor expressed on the B-cells surface to an antigen exposed on the surface of an antigen-presenting cell (APC). This in turn triggers a cascade of intracellular and intercellular events that leads to antibody secretion and pathogen attack by the complement system. Likewise, T-cell activation occurs via the interaction of an antigen on the surface of an APC with the T-cell receptor on the T-cell surface. Furthermore, T-cells recruitment to inflammatory/infected sites relies on the extravasation of T-cells from the bloodstream into tissue. Extravasation is initiated by a cytokine-regulated multistep adhesion process to the vascular epithelium followed by transmigration through the cell wall of blood vessels. Immunodeficiency and autoimmune diseases represent a misbalance in immune response. In all processes that can lead to abnormal immune response, e.g. altered lymphocyte activation, cell-adhesion, cell-migration and pathogen attack, the interaction of bio-molecules on the cell surface with binding partners in the extracellular environment is essential.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings and replicas of the photographs are not necessarily to scale. In certain instances, details that are not necessary for an understanding of the disclosure or that render other details difficult to perceive may have been omitted. It should be understood, of course, that the disclosure is not necessarily limited to the particular examples or embodiments illustrated or depicted herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
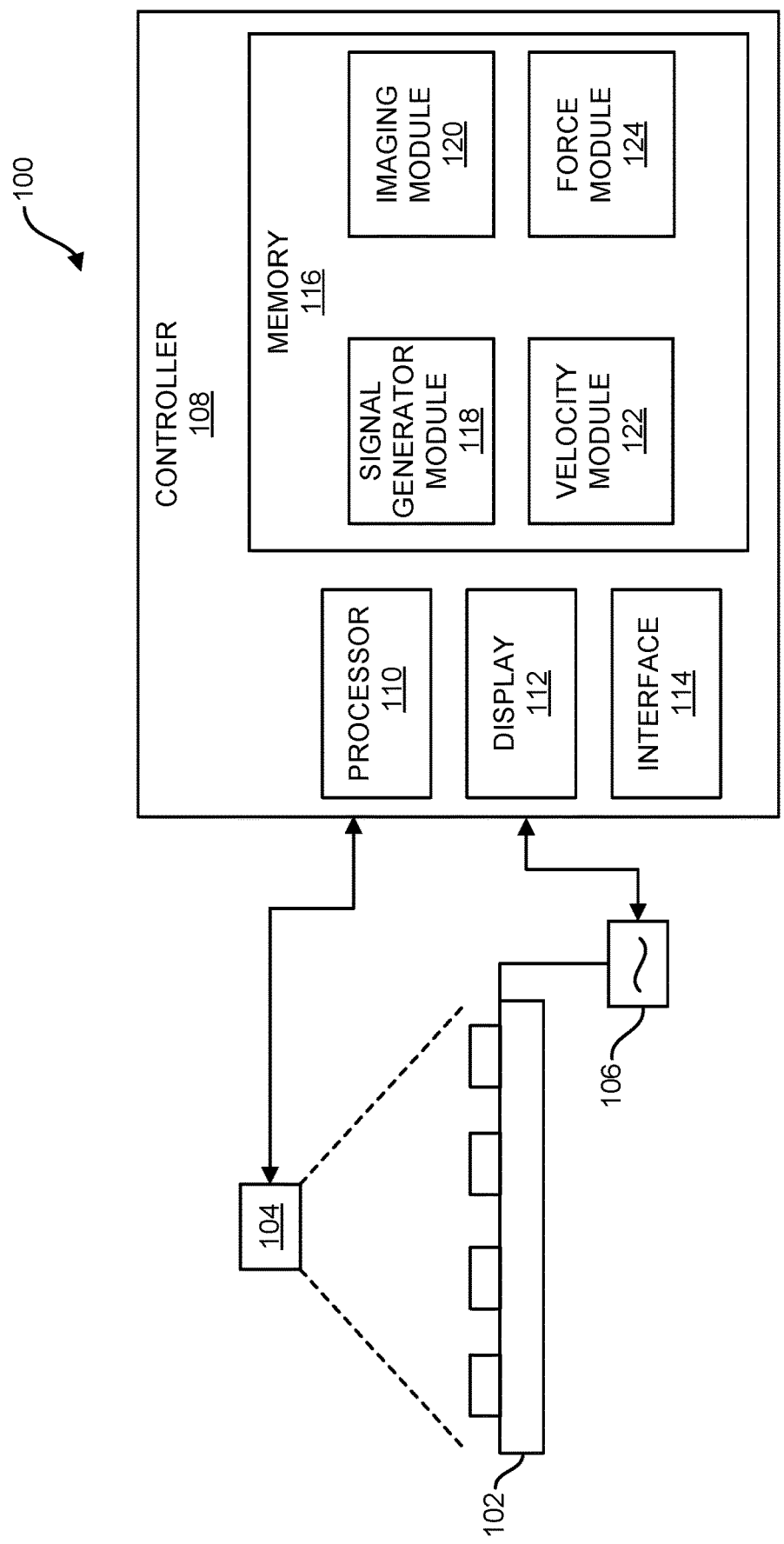
FIG. 1 illustrates a schematic view of an example of a system for determining a cell binding force according to the present disclosure.

Referring to FIG. 1, there is depicted a schematic view of an example of a system 100 for determining a cell binding force according to the present disclosure. The system 100 may include an acoustic device 102, an imaging device 104 configured to image the plurality of cell matrices, which are disposed in the plurality of open chambers 130 within the acoustic device 102. The system 100 may also include a signal generator 106 electrically coupled to the one or more acoustic generators, which are also disposed in the plurality of open chambers 130 within the acoustic device 102. Both the signal generator 106 and the imaging device 104 are electrically coupled to a controller 108, which is also included in the system 100. The signal generator 106 is capable of producing signals at a constant or variable amplitude with a frequency of between 1000 Hertz (Hz) and 500 Megahertz (MHz), including any range or increment therebetween.

The controller 108 comprises one or more processors 110, random access memory 116, and/or storage medium. In that regard, in some instances, the random access memory 116 is programmed to execute steps associated with the data acquisition and analysis described herein. Accordingly, it is understood that any steps related to data acquisition, data processing, instrument control, and/or other processing or control aspects of the present disclosure may be implemented by the computing systems using corresponding instructions stored on or in a non-transitory computer readable medium accessible by the computing device. In some instances, the controller 108 is a workstation or console device. In some instances, the controller 108 is portable (e.g., handheld, on a rolling cart, etc.). Further, it is understood that in some instances the controller 108 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure. The controller 108 may generate a visual representation of the input data and output data either of which is sent to the display 112. In some examples, the controller 108 and/or the display 112 may include a user input device (e.g., keyboard, mouse, touchscreen) or some other type of user interface 114.

As will be discussed in more detail herein, the memory 116 may store non-transitory computer readable medium, which included instructions corresponding to a signal generator module 118, an imaging module 120, a velocity module 122 and a force module 124. The signal generator module 118 may be configured to control the amplitude of the signal produced and emitted by the signal generator 106. The imaging module 120 may be configured to capture, interpret and/or analyze the images of the cell matrices. The velocity module 122 may be configured to estimate and/or determine the velocity of the stream of the suspension liquid based on the amplitude of the signal produced by the signal generator 106. The force module 124 may be configured to calculate a force at which one or more cells detach from one of the plurality of cell matrices based on the estimated velocity of the stream of the suspension liquid.

Figure 3:
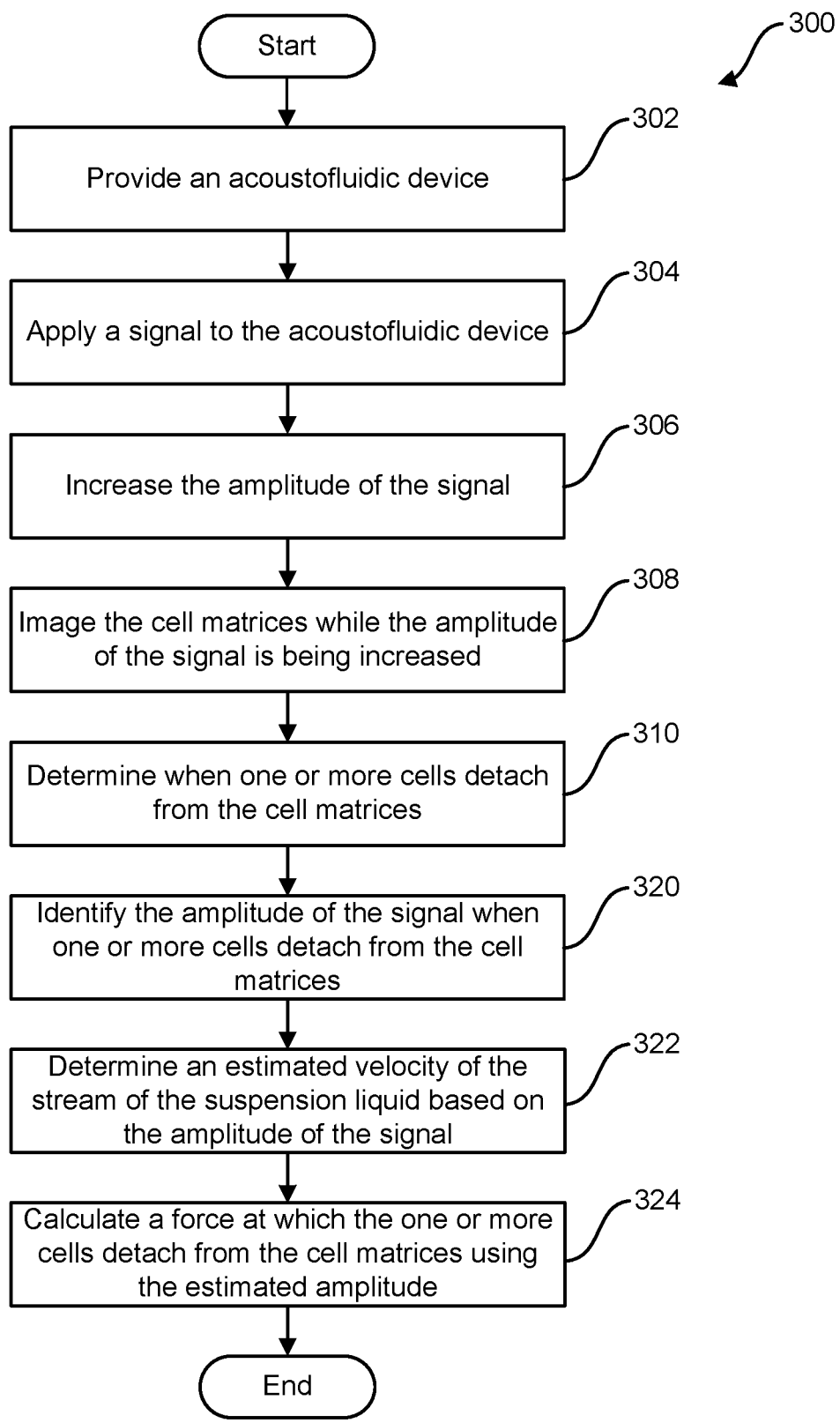
FIG. 3 illustrates a flow chart of an example of a method for determining a cell binding force according to the present disclosure.

Referring to FIG. 3, an example of a method 300 of determining a cell binding force of the present disclosure may be performed, at least in part, by the one or more processors 110, which executes the non-transitory computer readable medium instructions stored on the random access memory 116, whereupon providing an acoustic device 102 in step 302, execution of the instructions by the one or more processors to substantially simultaneously and/or in parallel cause(s): the application or delivery of a signal by the signal generator 106 to each of the open chambers 130 in the acoustic device 102 in step 304, an increase in amplitude of the signal in step 306, imaging the plurality of cells and/or cell matrices while maintaining or increasing the amplitude of the signal in step 308 for each of the open chambers 130, determining when one or more cells detach from one of the plurality of cell matrices in each of the open chambers 130 in step 310; identifying the amplitude of the signal when one or more cells detach from another cell or one of the plurality of cell matrices in each of the open chambers 130 in step 312, determining an estimated velocity of the stream of the suspension liquid based on the amplitude of the signal in each of the open chambers 130 in step 314, particularly when one or more cells detach from another cell or one of the plurality of cell matrices, and calculating a force at which one or more cells detach from another cell or one of the plurality of cell matrices in each of the open chambers 130 using the estimated velocity in step 316.

Figure 2A:
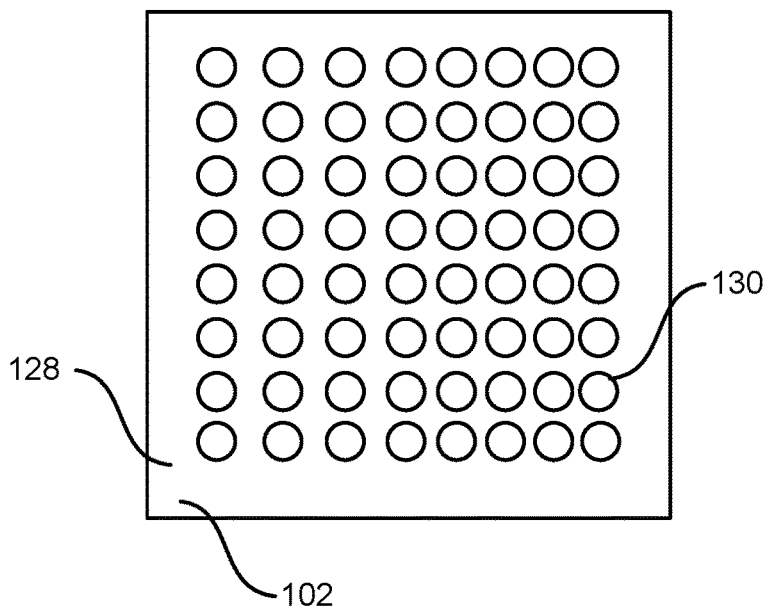
FIG. 2A illustrates a top view of an acoustic device depicted in FIG. 1.
Figure 2B:
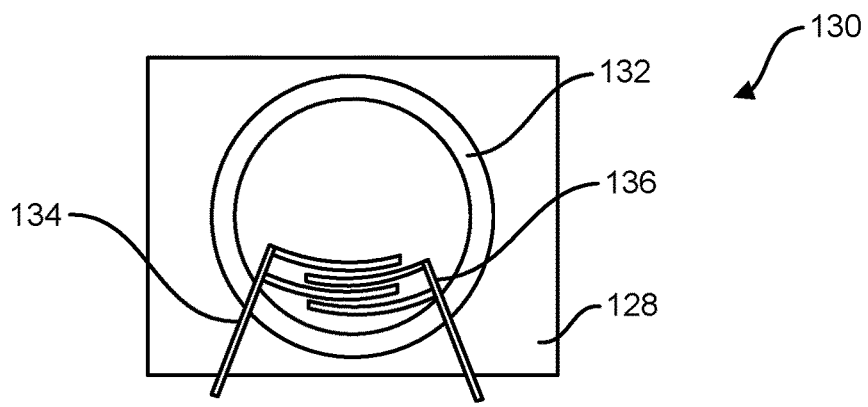
FIG. 2B illustrates an enlarged top view top of an open chamber of the acoustic device depicted in FIG. 2A.
Figure 2C:
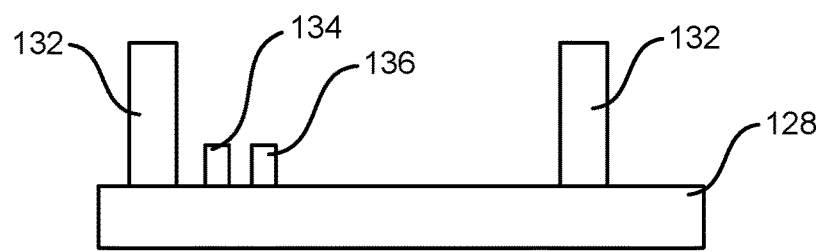
FIG. 2C illustrates an enlarged side view side of an open chamber of the acoustic device depicted in FIG. 2A.

Referring to FIGS. 2A, 2B and 2C, there is depicted the acoustic device 102 illustrated in FIG. 1. The acoustic device 102 may have a plurality of open chambers 130 disposed on a substrate 128. The substrate 128 may be a piezoelectric material, such as quartz or lithium niobite ($LiNbO_3$). Each open chamber 130 is formed by affixing one or more vertical walls or sides 132 to the substrate 128, wherein the walls 132 form a sealed area extending vertically from the substrate 128 while leaving the top of the chamber open and unsealed. The walls 132 may be constructed of a photoresist material such as SU-8, which is an epoxy-based negative photoresist material, or other photoresist materials. The open chamber 130 is depicted as a circular ring and has one wall 132. However, the present disclosure envisions the open chamber having an oval, triangular, rectangular, square or other polygon shape with one or more walls. Assuming the open chamber 130 is a circular ring, the diameter of the ring may be about 4 millimeters (mm), and the wall 132 may have a thickness of about 100 micron and a height of about 200 micron. The open chamber 130 may be formed on the lithium niobite using a soft lithography process.

The open chambers 130 are configured to retain fluid, such as a suspension fluid. As shown in FIGS. 2B and 2C, the acoustic device 102 may also include a means for producing a plurality of standing surface acoustic waves, such as a standing surface acoustic wave generator that includes a pair of acoustic wave generators to produce a stream within the open chambers 130. One example of a standing surface acoustic wave generator is an interdigital transducer (IDT), which is a device that comprises two or more electrodes 134, 136 deposited on the surface of a piezoelectric substrate 102 within or underneath each open chamber 130. Although only two electrodes are depicted in FIGS. 2B and 2C, additional electrodes, such as four, six, eight, ten, twelve, etc. electrodes may be included within an IDT. Additionally, each electrode may have a plurality of fingers, such as two, four, six, eight, ten, twelve, etc. fingers or pairs of fingers. Continuing to refer to FIGS. 2C and 2C, both electrodes 134, 136 are arch-shaped and disposed radially offset from the center of the open chamber 130. That is, the electrodes 134, 136 are disposed between the wall 132 and the center of the open chamber 130. Hence, due to the arch-shape and disposition of the electrodes, the electrodes have a focal point, thereby creating a focusses IDT. Although FIGS. 2B and 2C, illustrate a means for producing a plurality of standing surface acoustic waves, such as a standing surface acoustic wave generator, the acoustic wave generator could alternatively produce a bulk acoustic wave, which in turn could produce a stream within the open chambers 130.

Each electrode 134, 136 may be constructed of photoresist material and formed by an interlocking comb-shaped array that includes a plurality of separated fingers. As shown in FIG. 2B, the electrodes 134, 136 are arched shape, and the arch-shaped fingers from one electrode intertwine with the arch-shaped fingers from the other electrode. When a radio frequency (RF) or an alternating current (AC) signal is applied to the electrodes, the piezoelectric substrate 102 vibrates at the frequency of the RF signal. The vibration creates a set of traveling standing surface acoustic wave (SAW) as a Rayleigh wave on the surface of the piezoelectric substrate 102. A SAW also propagates along fluid disposed over the surface of the piezoelectric substrate 102. As such, it may be desirable, to interpose a liquid layer (not shown), comprised of water or oil (e.g., mineral oil, olive oil, etc.), between the piezoelectric substrate 102 and the open chamber 130. Once the SAW interferes with the liquid within the open chamber, a localized stream within the liquid is created.

The shape of SAWs, such as the resulting frequency, amplitude, and wave-front orientation of the acoustic waves, is at least partially dependent upon the pattern and dimensions of the electrodes, the RF signal (e.g., power of the signal), and the piezoelectric material, including the speed of sound in the material. For example, the frequency of the SAWs is defined by $v/\lambda$, where v is the speed of sound in the piezoelectric material and $\lambda$ is the acoustic wavelength. The wavelength ($\lambda$) of SAW is dependent on the width of the fingers 126 of the electrodes, as well as the spacing between fingers. It may be desirable to adjust the frequency or wavelength of the SAW. As such, referring to FIG. 1A, it may desirable for the acoustic device 100 to include a signal generator 106, which produces the RF or AC signal, to be electrically coupled to a controller 108 that has the ability to alter the amplitude, frequency and/or wavelength of the RF or AC signal. The controller 108 may be generally representative of any device suitable for performing the processing and analysis techniques discussed within the present disclosure.

Figure 6A:
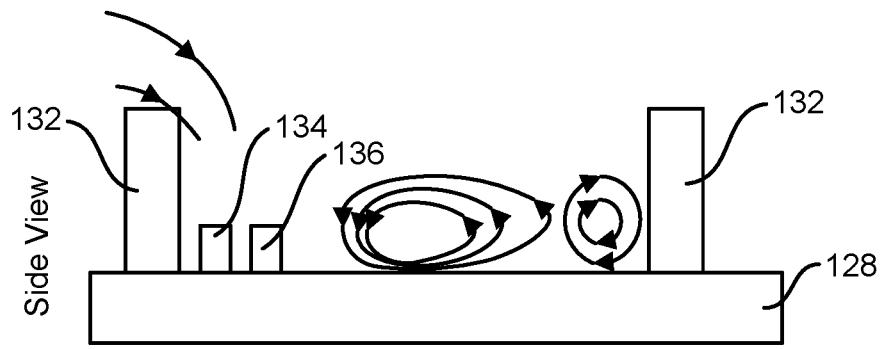
FIG. 6A illustrates a schematic view of a stream of fluid created by the acoustic device depicted in FIG. 1, wherein the stream and acoustic device is depicted in and y-z plane, as shown in FIG. 2B.
Figure 6B:
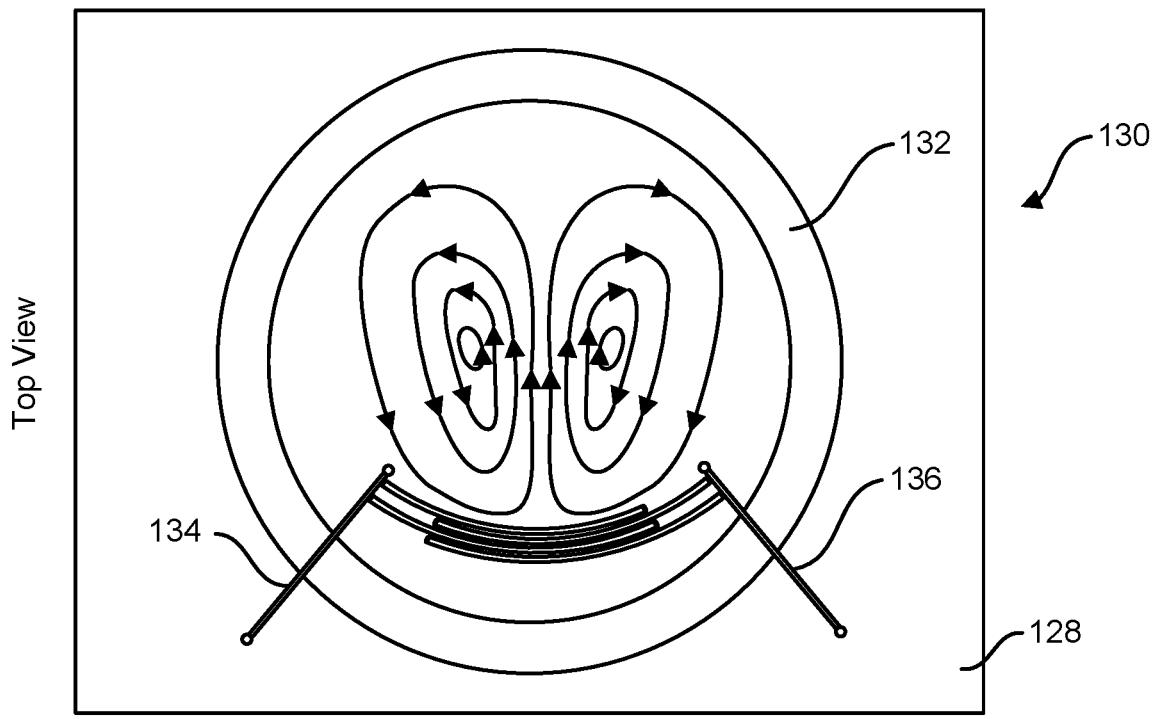
FIG. 6B illustrates a schematic view of a stream of fluid created by the acoustic device depicted in FIG. 1, wherein the stream and acoustic device is depicted in and x-y plane, as shown in FIG. 2C.

Referring to FIGS. 6A and 6B, there is shown a side view schematic and a top view schematic, respectively, of acoustic streaming of the fluid within each of the chambers 130. The side view shown in FIG. 6A depicts the vertical direction that the fluid travels, and the top view shown in FIG. 6B depicts the horizontal direction that the fluid travels once the IDTs are activated at a resonance frequency, such as about 37.4 MHz, due to the creation of a highly localized acoustic field produced above the IDT. As shown in these figures, the localized streaming provides an ideal area with a uniformly distributed streaming pattern created by the streaming fields. Using the controller 108 to digitally control the signal generator 106 to produce the RF or AC signal, provides the system 100 with the capability precisely create and sustain a uniform streaming pattern. Referring to FIG. 6A, which is a side view of the streaming pattern in an acoustic device, the stream flows down to the edge of the focused IDT (electrodes) along the y-z plane, rotates counter-clockwise towards the focused IDT (electrodes), and forms a streaming vortex in the vertical plan. Referring to FIG. 6B, which is a side view of the streaming pattern, two symmetric fluids jets form along a central symmetrical axis of the IDT on the x-y plane from the center of the electrode(s). The two symmetrical jets interact with the boundary formed by side wall 132, recirculate back to the front sides of the IDT, and finally complete a two-vortex streaming pattern. As such, there is an area of fluid between the two symmetrical vortex jets, wherein the fluid in this area moves distally from the IDT.

Figure 4:
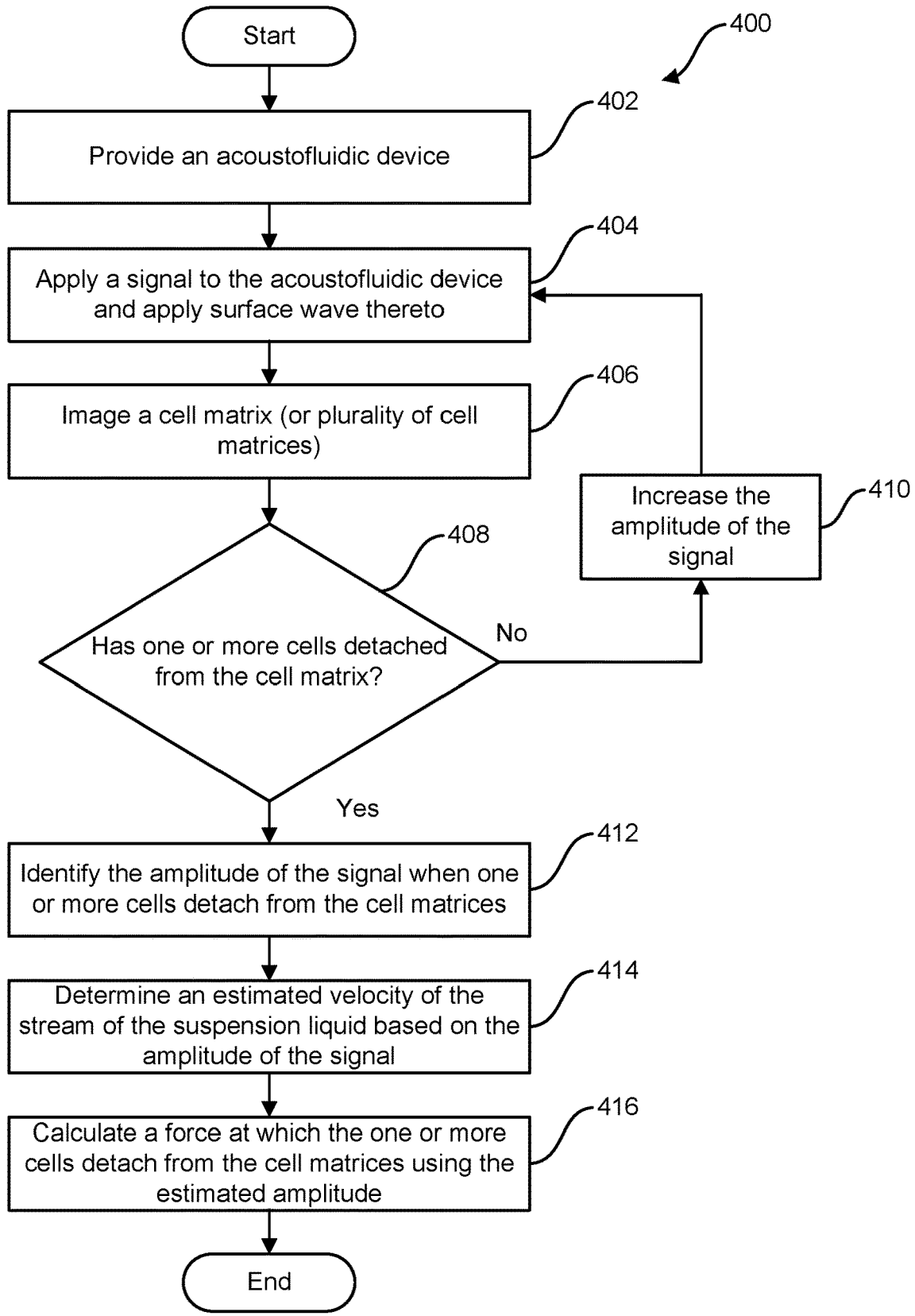
FIG. 4 illustrates a flow chart of another example of a method for determining a cell binding force according to the present disclosure.

As mentioned above, FIG. 3 illustrates an example of a method 300 of determining a cell binding force (or a cell detachment force) based on cells adhered to the substrate in the area of interest between the two symmetrical vortex jets. The method of the present disclosure may be performed, at least in party, by the one or more processors 110 by executing the non-transitory computer readable medium instructions stored on the random access memory 116. Referring to FIG. 4, there is depicted an alternative method 400 of determining a cell binding force of the present disclosure may be performed, at least in party, by the one or more processors 110 by executing the non-transitory computer readable medium instructions stored on the random access memory 116. For example, whereupon providing an acoustic device 102 in step 402, execution of the instructions by the one or more processors cause(s): the signal generator 106 to produce and send a signal to the acoustic device 102 in step 404, and the imaging device 104 to image the plurality of cell matrices while maintaining the amplitude of the signal in step 408. Next, the imaging module 118 determines whether one or more cells has detached from one of the plurality of cell matrices in step 408. If the imaging module 118 determines that one or more cells has not detached from one of the plurality of cell matrices, the amplitude (and/or frequency) of the signal is increased in step 410. Alternatively, if the imaging module 118 determines that one or more cells has detached from one of the plurality of cell matrices, the amplitude (and/or frequency) of the signal is maintained and identified in step 412. Based on the identified amplitude (and/or frequency of the signal), an estimated velocity of the stream of the suspension liquid based on the amplitude of the signal is determined in step 314, and a force at which one or more cells detach from one of the plurality of cell matrices using the estimated velocity in step 316.

Figure 5A:
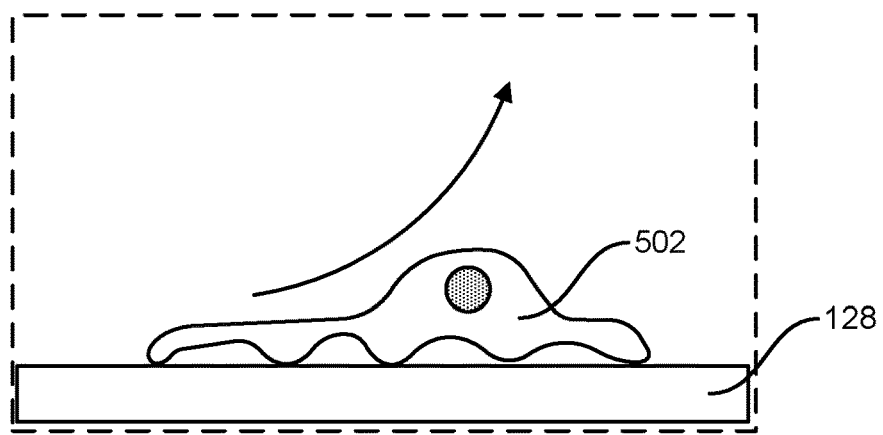
FIGS. 5A, 5B and 5C illustrate the cell detachment process using a system and a method according to the present disclosure.
Figure 5B:
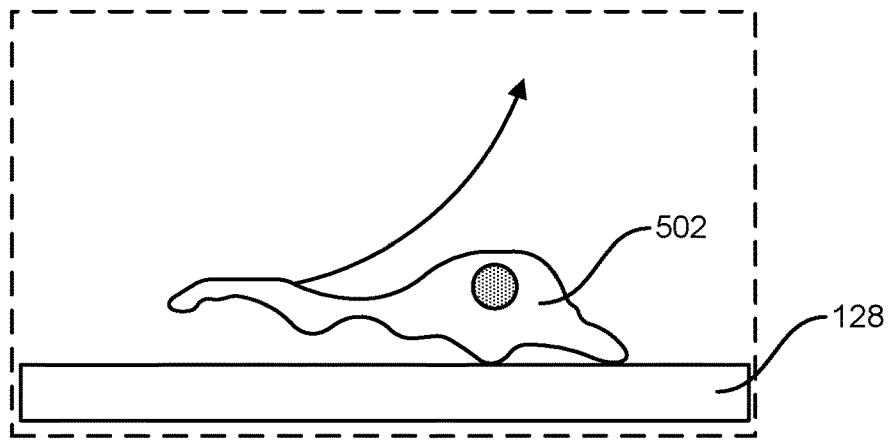
Figure 5C:
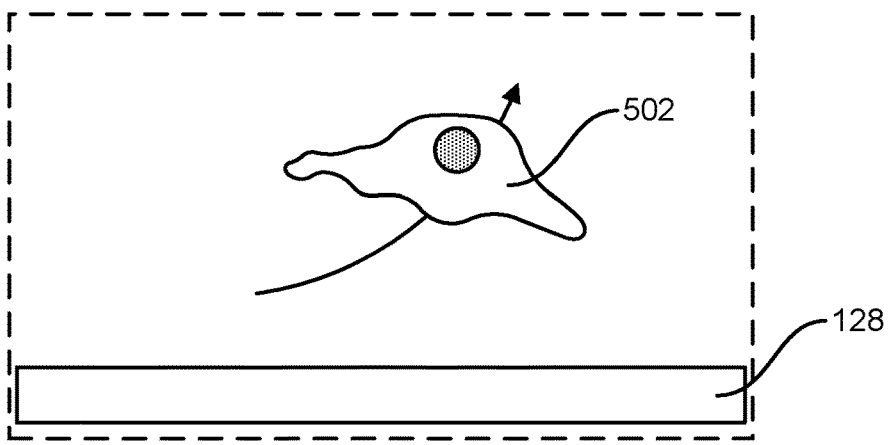

Referring to FIGS. 5A, 5B and 5C, there is depicted an illustrative example of a cell detachment process using a system and a method according to the present disclosure. Referring again to FIGS. 6A and 6B, once the IDT(s) are activated, the IDTs create a highly localized acoustic field, thereby creating a localized stream of fluid as depicted by the arrows in FIGS. 5A, 5B and 5C. The Stokes drag force induced by the streaming ruptures the cell-matrix junction, as shown in FIG. 5B and detaches cells 502 from a fibronectin-functionalized substrate 128, as shown in FIG. 5C. Due to the strongly localized streaming, the Stokes drag force applied on cells measures up to tens of nanonewtons. By tuning the input power of focused IDT(s), different sized forces can be applied to cells to detach the cells from substrate in real time. As a result, detailed force maps of cell-matrix interactions can be measured during the process of acoustic detachment.

In principle, once the focused IDT is activated at a resonance frequency, such as a frequency of about 37.4 MHz, a localized acoustic field is produced in the liquid domain above the IDT. As a result, highly localized acoustic streaming is induced via the interface of the piezoelectric substrate and liquids. The Stokes drag force generated by the acoustic streaming ruptures the cell-matrix junction and detaches cells from the fibronectin-functionalized substrate as shown in FIGS. 5A, 5B and 5C. The localized streaming provides uniform distributed streaming fields, thereby in turn providing uniform shear force for all the cells within this area. By generation of digitalized streaming via a programmable radio frequency (RF) signal, the Stokes drag force can be produced and applied to the adherent cells within the area of interest with precise control of the force level and duration to detach the cell 502 from the substrate 128. Taking advantage of time-lapse imaging, the cell adhesive force, which creates attachment between the cell and the substrate, can be measured by recording and analyzing the cell detachment and Stokes drag force induced by digitalized streaming. As will be discussed in more detail below, force maps of cell-matrix interactions were measured during the process of acoustic detachment. Because of the unique design of the digital acoustic device and the associated technique of using the acoustic device can provide several advantages. For example, the digital acoustic device can (i) generate uniform and localized acoustic streaming by introducing a focused IDT within an open microfluidic chamber, (ii) reduce the acoustic energy loss and acoustic interference with the microfluidic channel well, (iii) generate a wide range of streaming speeds up to 10 mm/s and/or a short dynamic response time of less than 100 ms (particularly with a programmable RF signal produced by the signal generator and controlled by the controller), (iv) provide a measure of cell-matrix adhesion with a force range up to several nN and a force switching time less than 100 ms, which is better than existing acoustic radiation force-based or hydrodynamic-flow-based microfluidic methods, and (v) is compatible with conventional cell culture due to its open-chamber configuration.

As mentioned above with respect to FIGS. 3 and 4, after identifying the amplitude of the signal when one or more cells detach from one of the plurality of cell matrices is determined, an estimated velocity of the stream of the suspension liquid based on the amplitude of the signal is determined and a force at which one or more cells detach from one of the plurality of cell matrices using the estimated velocity is calculated. To profile the cell-matrix interaction, it is important to understand the mechanism by which focused IDTs detach cells from the substrate, which is tantamount to detaching cells from other cell matrices. The mechanism creates a set of traveling surface acoustic waves (SAWs) as a Rayleigh wave was produced after applying an RF signal to the focused IDT. The exponential decay of the amplitude with the depth of the substrate allowed the wave to confine most of its energy to the surface. Once the wave interfered with the liquid within the open chamber, localized streaming was created in the liquid.

Regarding the step of estimating a velocity of the stream of the liquid, an acoustic streaming simulation model. That is, a numerical model was used to predict the three-dimensional pattern of acoustic streaming. This model considered the effects of the transverse and longitudinal vibrations on the liquid and the interface between the substrate and the liquid layer in the chamber. Both the transverse and longitudinal vibrations attenuate in a thin boundary layer close to the substrate, resulting in a specific streaming pattern in the fluidic layer. The numerical results described the streaming vortex and the distribution are in three dimensions. The schematic and simulation of the acoustic streaming were described herein above with respect to FIGS. 6A and 6B. The arrows show the acoustic streaming direction. Along the vertical direction, the acoustic streaming flowed down the edge of the focused IDT, rotated counterclockwise, rose from the substrate, and then formed two streaming vortexes. Along the horizontal direction, two symmetric fluids jetted along the symmetric axis of the IDT from the edge of electrodes, interacted with the side boundary, recirculated back along the electrodes of the IDT, and then completed a second round of the streaming pattern.

Calculation of Shear Force on a Single Cell

The Stokes drag force acting on an adherent cell can be calculated based the equation:

$$F = 6\pi\mu r v$$

where $\mu$ is the dynamic viscosity of the sucrose solution, r is estimated radius of the adherent cell, and v is the acoustic streaming velocity.

The streaming drag force was calculated based on the measured streaming velocity.

As discussed above, the IDT(s) and particularly the electrodes have a focal point, thereby creating a focusses IDT. It is the focused electrodes and IDT(s) that create generally symmetrical vortexes of the steaming fluid, and utilizing a circular-shaped open chamber enhances the symmetry of vortexes, as well as the control of the area of interest includes the adjacent vortexes, the area between the vortexes and/or the intersection of the adjacent vortexes. Although the figures of the present disclosure depict focused electrodes and/or focused IDTs and creating multiple or symmetrical vortexes, the present disclosure envisions utilizing one or more non-focused electrodes and/or IDTs to create the acoustic streaming of the fluid. For example, the electrodes and/or IDTs could be configured and arranged within an open chamber to create a unidirectional stream of fluid therein.

Figure 7A:
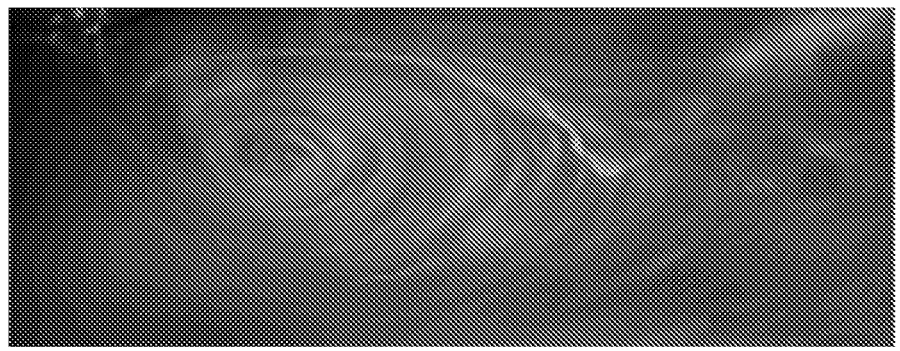
FIG. 7A illustrates a set of stacked images of a 2 micron particle based upon experimental results depicting a trajectory upon activating the acoustic device depicted in FIG. 1, wherein the trajectory of the stream of fluid is depicted in and y-z plane, similar to that as shown in FIG. 2B.
Figure 7B:
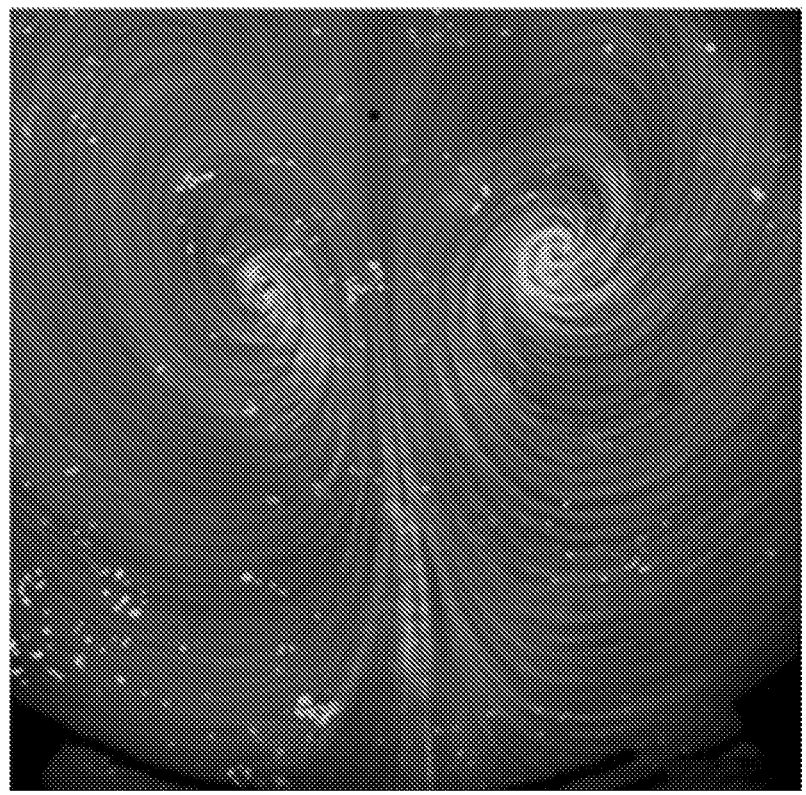
FIG. 7B illustrates a set of stacked images of a 2 micron particle based upon experimental results depicting a trajectory upon activating the acoustic device depicted in FIG. 1, wherein the trajectory of the stream of fluid is depicted in and x-y plane, similar to that as shown in FIG. 2C.
Figure 7C:
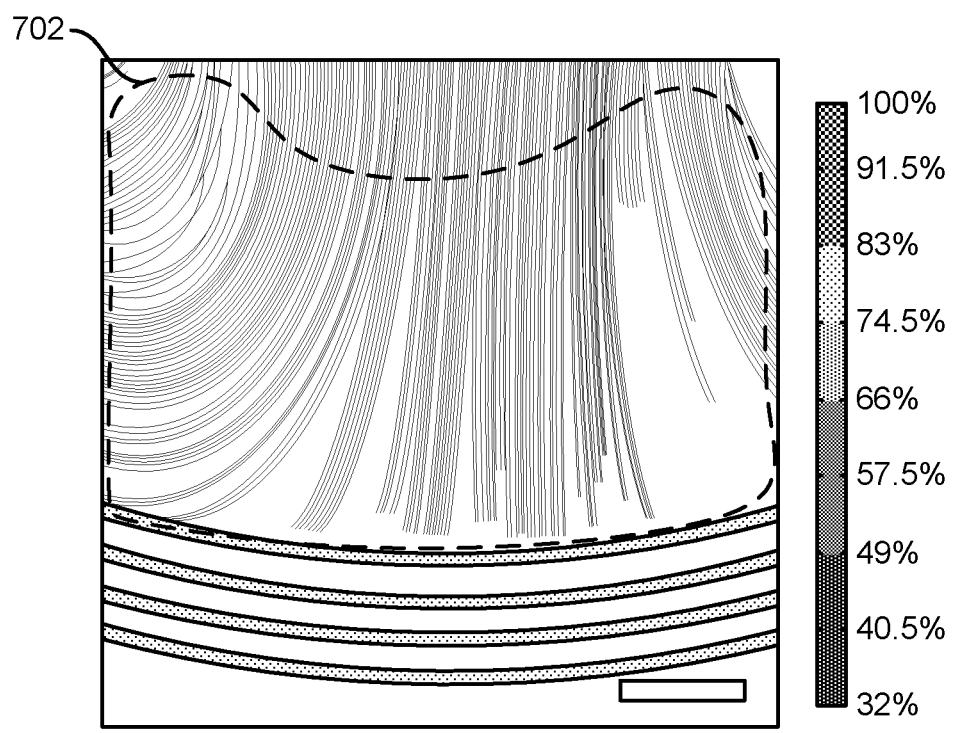
FIG. 7C illustrates an enlarged view of a portion of the trajectory shown in FIG. 7B, namely an area of interest of the trajectory of the stream of fluid.

Again, the model considered the effects of the transverse and longitudinal vibrations on the liquid and the interface between the substrate and the liquid layer in the chamber. Both the transverse and longitudinal vibrations attenuate in a thin boundary layer close to the substrate, resulting in a specific streaming pattern in the fluidic layer. The numerical results described the streaming vortexes and the distribution are in three dimensions. The arrows show the acoustic streaming direction, with streaming velocity indicated by background designs on the right side of the scale, which are indicative of the higher and maximum velocities, and the designs on the left side of the scale, which are indicative of the lower and minimum velocities. Along the vertical direction, the acoustic streaming flowed down the edge of the focused IDT, rotated counterclockwise, rose from the substrate, and then formed two streaming vortexes. Along the horizontal direction, two symmetric fluids jetted along the symmetric axis of the IDT from the edge of electrodes, interacted with the side boundary, recirculated back along the electrodes of the IDT, and then completed a second round of the streaming pattern. Referring to FIG. 7C, there is illustrated an area of interest 702 in the acoustic streaming field which has a relatively uniform streaming speed, particularly the area marked by item 702 and having a 60.1% to 82.9% streaming speed. It is this area of interest between and/or the adjacent vortexes and the intersection of the vortexes that was used to calculate the estimated velocity of the stream of the suspension liquid and the force at which one or more cells detach from one of the plurality of cell matrices using the estimated velocity is calculated.

The model was verified by comparing the simulation of the model to experimental results, namely an experiment designed and performed to investigate SAW-induced acoustic streaming within the fluidic chamber. The experiment began as follows:

Experiment

The Acoustic Device. The acoustic device 102 used in the experiment was designed and fabricated using the protocol discussed previously herein. Particularly, referring to FIGS. 2A, 2B and 2C as a reference, the acoustic device 102 had a plurality of open chambers 130 disposed on a lithium niobite substrate 128, which was about 500 micron thick and polished on both sides. Each open chamber 130 was constructed of a circular-shaped SU-8 photoresist 132 having a diameter of about millimeters (mm), a wall thickness of a about 100 micron and a wall height of about 200 micron. Within each open chamber 130 was a pair of focused IDTs fabricated using a standard soft-lithography and lift-off technique. The focused IDTs were designed as eight (8) pairs of finger electrodes, wherein the width of each finger and the gap between each finger was the same, namely 25 micron. Each finger, and therefore the electrodes, had a focusing angle of about fifty seven degrees (57°), although other focusing angles could have been used. The fingers were made by depositing two metal layers on a 128° YX-propagation lithium niobate substrate (with a thickness of 500 double-side polished). One metal layer was made of chromium (Cr) and had a thickness of about 100 nanometers (nm) and another layer was made of gold (Au) and had a thickness of about 500 nm. The fingers may have additional layers of material to isolate the electrodes from the substrate or fluid.

Cell Culture. Breast cancer cells (MCF-7, MDA-MB-231, and MCF-10A) were purchased from American Type Cell Culture (ATCC, Manassas, VA, USA) and cultured in Dulbecco's modified Eagle's medium (Corning, NY, USA) supplemented with 10% fetal bovine serum (Sigma-Aldrich, St. Louis, MO, USA), 100 U/mL penicillin, and 100 μg/mL streptomycin (Invitrogen, Millersburg, PA, USA) in a humidified incubator at 5% $CO2$ and 37° C.

Live/Dead Staining. Live/dead staining was conducted using the Live/Dead Kit (Invitrogen) following the manufacturer's instructions. The cells were stained in a medium supplemented with 2 μM carboxyfluorescein succinimidyl ester and 4 μM ethidium homodimer for 4 h. And the cells were cultured in the device for 30 min and the adhesion strength was measured (from 6 to 51 peak-to-peak voltage (Vpp), 3 Vpp interval). The staining results were visualized by an inverted fluorescence microscope (IX81, Olympus). Final cell viability was analyzed using ImageJ to account for area of live/dead cells.

Introduction of Fluorescent Particles. A plurality of 2 μm fluorescent polystyrene particles were introduced to the acoustic device 102. The particles were first uniformly located on the surface of the substrate 128. Once the SAW was applied, the particles were flowing to form two symmetric streaming vortexes along the symmetric axis of the IDT in the x-y plane. Along the vertical axis, a triprism was used to help visualize the movement of particles. The microscope was focused on the symmetric axis of the focused IDT. Once the SAW was applied, the particles rose up from the substrate, rotated counterclockwise, flowed down to the focused IDT, and formed a vortex.

Results

Force Analysis. To calculate the rupture force of the cell-matrix junction by acoustic streaming, the streaming speeds were quantified for different RF signal voltage inputs. First, it is desirable that an area with uniformly distributed streaming is determined. Referring to FIGS. 7A and 7B, numerical results showed a scalloped area close to the focused IDT, with an almost identically colored streaming pattern. That is, the experimental results showing the acoustic streaming pattern by tracking the trajectories of 2 μm polystyrene particles, as shown in FIGS. 7A and 7B.

Again, a plurality of fluorescent polystyrene particles were used as markers to trace streaming patterns. A sequence of images was captured using a complementary metal oxide semiconductor (CMOS) camera at time intervals of 10 ms (100 fps). The streaming speed was then analyzed and calculated by the Trackmate plugin of ImageJ software. Trajectories of the fluorescent polystyrene particles showing the streaming speed distribution can be seen in FIG. 7C. As shown in FIGS. 7A, 7B and 7C, the area with uniformly distributed streaming is the area between the vortexes. For this experiment and example, the area of interest includes the adjacent vortexes, the area between the vortexes and/or the intersection of the adjacent vortexes. As discussed above, the IDT(s) and particularly the electrodes have a focal point, thereby creating a focusses IDT. It is the focused electrodes and IDT(s) that create generally symmetrical vortexes of the steaming fluid, and utilizing a circular-shaped open chamber enhances the symmetry of vortexes, as well as the control of the area of interest includes the adjacent vortexes, the area between the vortexes and/or the intersection of the adjacent vortexes.

Again, the transverse and longitudinal vibrations on the liquid and the interface between the substrate and the liquid layer in the chamber attenuate in a thin boundary layer close to the substrate, resulting in a specific streaming pattern in the fluidic layer. The numerical results described the streaming vortexes and the distribution are in three dimensions. The arrows show the acoustic streaming direction, with streaming velocity indicated by background designs on the right side of the scale, which are indicative of the higher and maximum velocities, and the designs on the left side of the scale, which are indicative of the lower and minimum velocities. Along the vertical direction, the acoustic streaming flowed down the edge of the focused IDT, rotated counterclockwise, rose from the substrate, and then formed two streaming vortexes. Along the horizontal direction, two symmetric fluids jetted along the symmetric axis of the IDT from the edge of electrodes, interacted with the side boundary, recirculated back along the electrodes of the IDT, and then completed a second round of the streaming pattern. Referring again to FIG. 7C, there is illustrated an area of interest 702 in the acoustic streaming field which has a relatively uniform streaming speed, particularly the area marked by item 702 and having a 60.1% to 82.9% streaming speed. It is this area of interest between and/or the adjacent vortexes and the intersection of the vortexes that was used to calculate the estimated velocity of the stream of the suspension liquid and the force at which one or more cells detach from one of the plurality of cell matrices using the estimated velocity is calculated.

Figure 8:
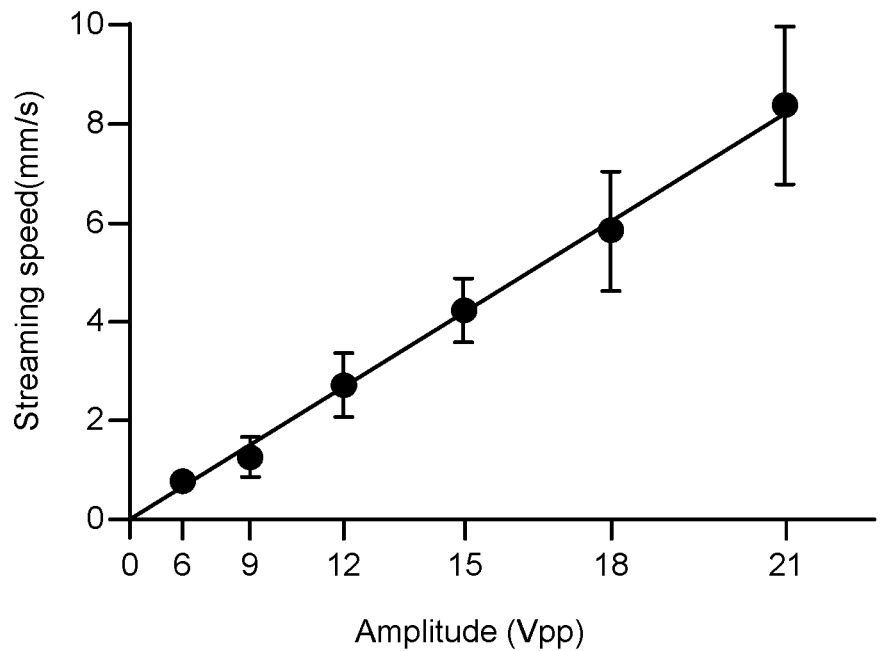
FIG. 8 is a graph illustrating the dependence of the acoustic streaming speed on the amplitude of the signal from the signal generator.
Figure 9:
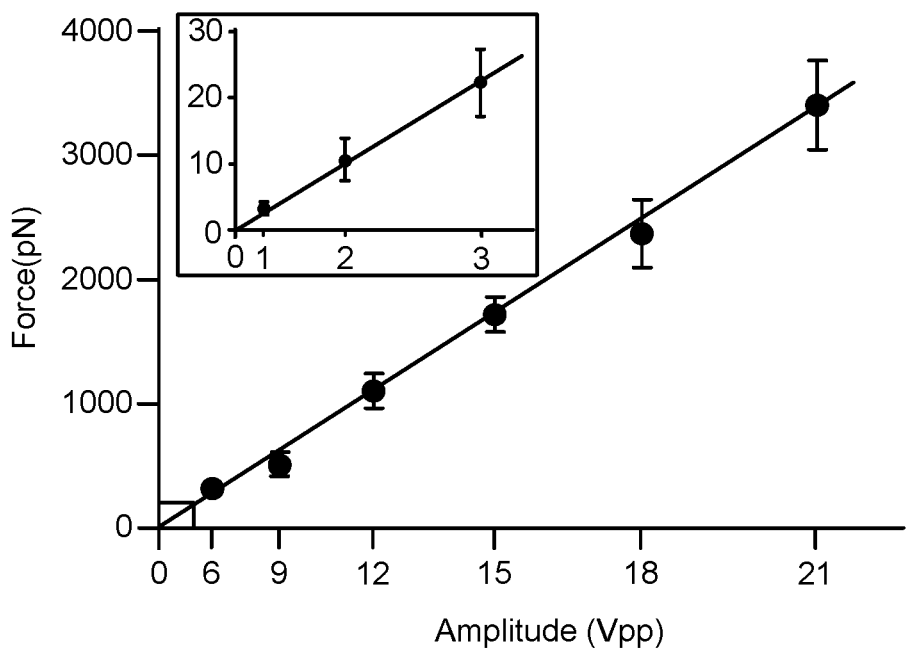
FIG. 9 is a graph illustrating the dependence of Stokes drag force on the amplitude of the signal from the signal generator, and in turn the acoustic streaming speed.

The dependence of the streaming speed in area of interest 702 was investigated relative to the amplitude of the input peak-to-peak voltage (Vpp) provided to the signal generator. The fluorescent polystyrene particles in the area of interest 702 were tracked using different signal amplitude inputs for five repetitions and calculated the average streaming speed and standard deviation (trajectories last for at least 5 frames). The final streaming speed versus input amplitude was plotted as shown in FIG. 8, which shows that trapping velocities increased gradually in a squared trend as the input peak-to-peak voltage increased. The streaming speed has a squared relationship with amplitude input, and our experimental results showed the squared trend. The curve was fitted quadratically to account for streaming speed when the amplitude was larger than 21 Vpp. Monitoring of the streaming speed can be achieved by tuning the amplitude of the input signal. To determine the adherence strength of cells using the acoustic detachment method of the present disclosure, the Stokes drag force on cells was calculated under different amplitude inputs (using the Force equation included hereinabove). The calculated Stokes drag force on adherent cells versus amplitude input is shown in FIG. 9.

Figure 10A:
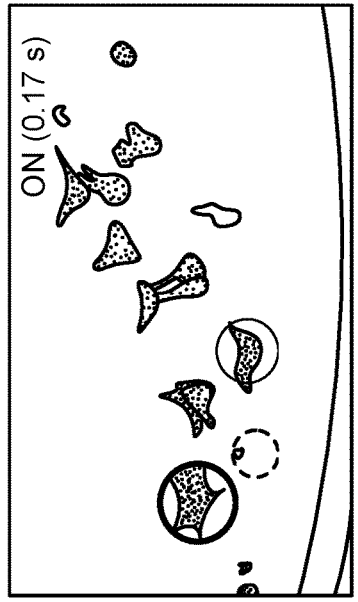
FIGS. 10A, 10B, 10C and 10D are black and white replicas of photographs of a plurality of cell matrices undergoing a detachment process when the acoustic device is in the ON position and streaming occurs within an open chamber.
Figure 10B:
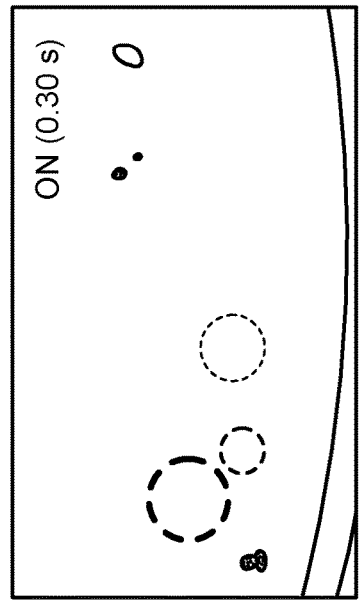
Figure 10C:
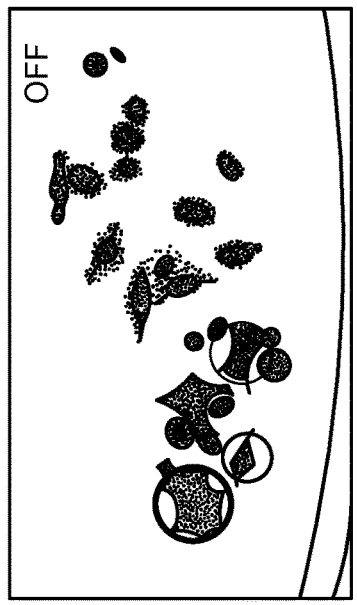
Figure 10D:
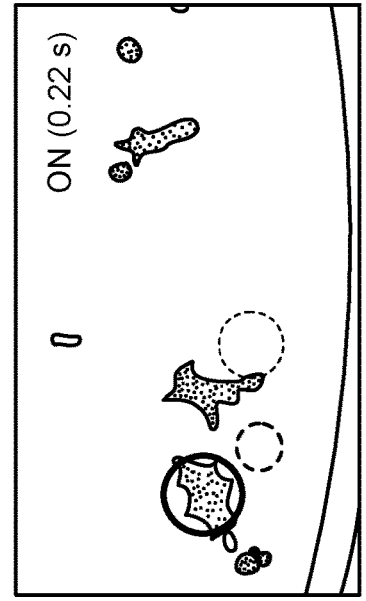
Figure 11B:
FIGS. 11A, 11B, 11C and 11D depict cells attached to the substrate, and as the amplitude of the signal(s) increase, the cells gradually detach from the substrate.
Figure 11D:
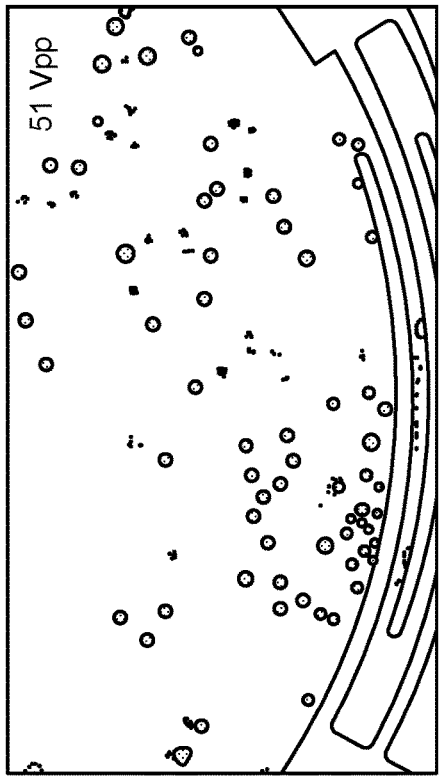
Figure 11A:
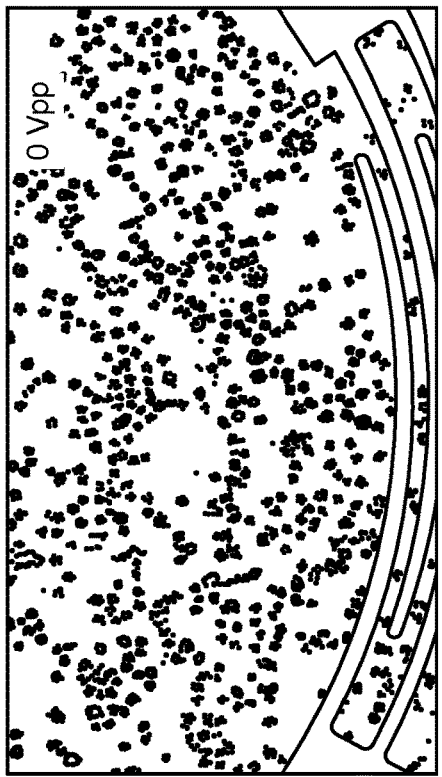
Figure 11C:
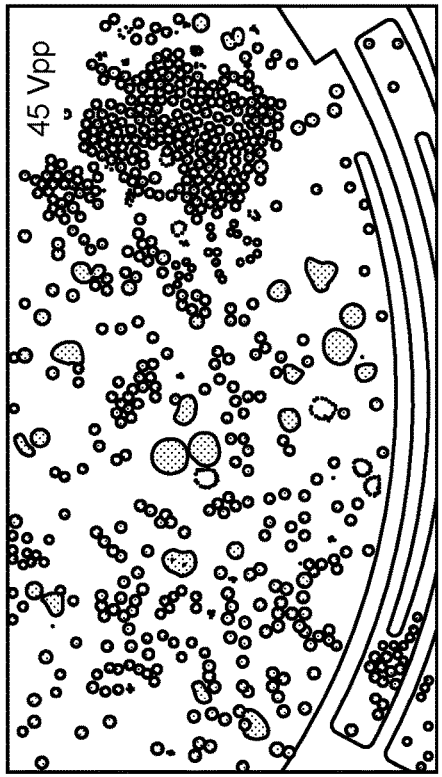

Measurement of Cell-Matrix Adhesion. On the basis of the numerical model and experimental results of an acoustic streaming field, adherent MDA-MB-231 cells were detached from a fibronectin-functionalized substrate. The bottom surface, namely the substrate, of the open chambers were coated with fibronectin to mimic the extracellular matrix (ECM) lining the endothelium of blood vessels. MDA-MB-231 cells were loaded into the open chamber and allowed to settle down on the fibronectin-coated bottom surface. After a 1-h incubation, a pulse surface acoustic wave (frequency=37.4 MHz, power=57 Vpp, duration=1.5 s, about 16 nN) was applied to detach adherent cells. After a 1-h culture, MDA-MB-231 cells first adhered and then spread out on the fibronectin-coated surface, as shown in FIG. 10A. For example, the solid circles in FIG. 10A identify, MDA-MB-231 cells adhered to the fibronectin-coated surface. When the SAW was applied to the device, a strong localized streaming was generated in the fluid domain. Stokes drag force induced by the flow gradually detached the cells in the streaming field, and all adherent cells were detached within 1 second. Referring to FIGS. 10B, 10C and 10D, the solid circles identifying the adhered cells in FIG. 10A, are progressively detached over time (e.g., from 0.17 seconds in FIG. 10B, to 0.22 seconds in FIG. 10C, to 0.30 seconds in FIG. 10D) and indicated by dashed circles in the same area. The viability of MCF-7 cells was tested as (82.3±5.4%) before the acoustic detachment and as (79.8±7.5%) after the acoustic detachment. Localized streaming, therefore, is capable of detaching fully adherent cells on the fibronectin-coated surface. Similarly, localized streaming is capable of detaching fully adherent cells from cell-matrices.

Figure 12:
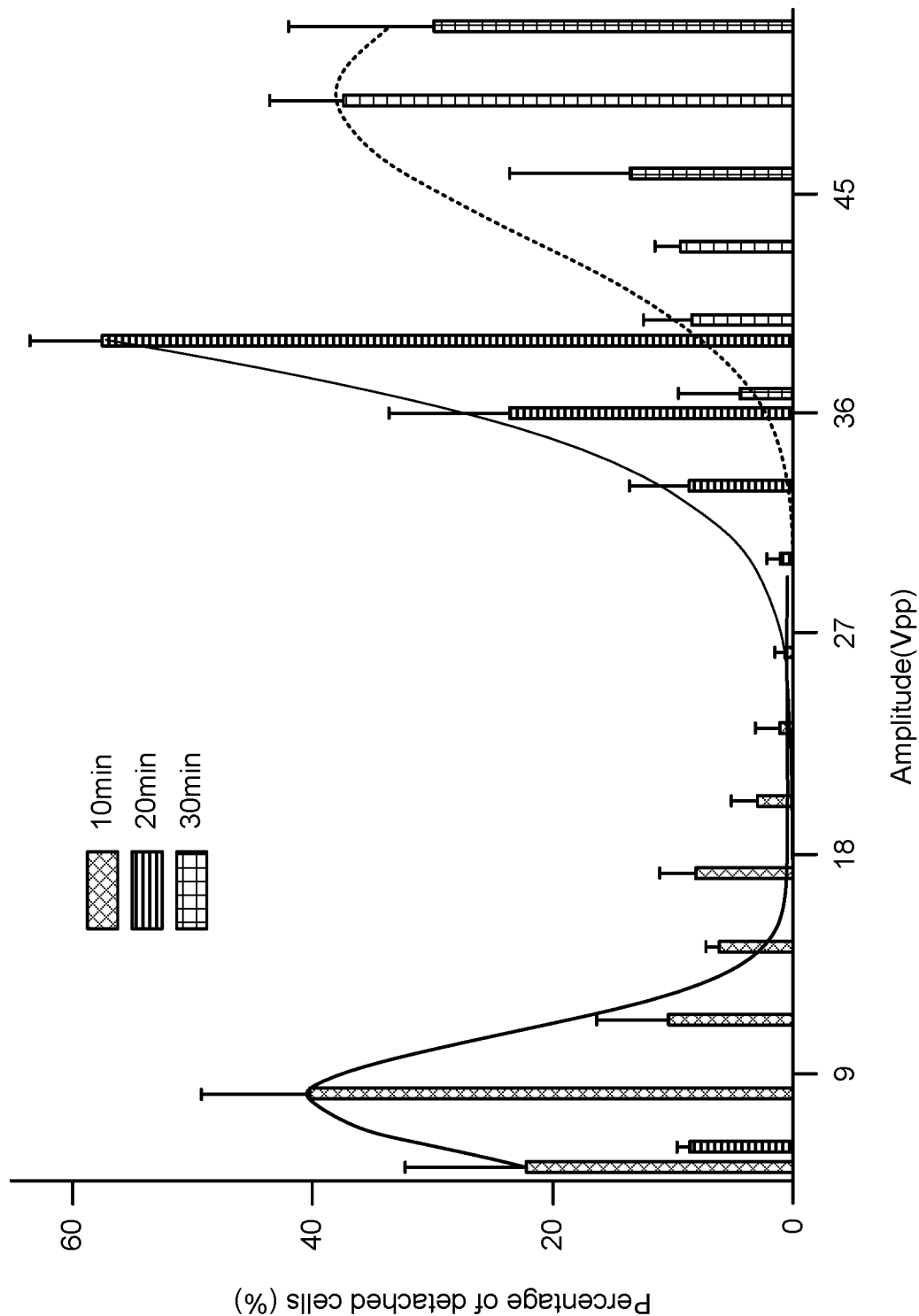
FIG. 12 illustrates a graph of the correlation between the percentage of detached cells, the signal amplitude and the time the cells were cultured.

Kinetics of Cell-Matrix Adhesion. After successfully measuring the cell adhesive force, the kinetics of cell-matrix adhesion of MCF-7 breast cancer cells were explored using the acoustic device 102 and method(s) of the present disclosure. MCF-7 cells for 10, 20, and 30 min were cultured in the open chambers of the acoustic device, and rupture forces of these cells were subsequently calculated. To quantify the kinetics of tumor cell adhesion to fibronectin, a 1.5 second acoustic pulse was applied by the signal generator to the acoustic device every 3 seconds. That is, an acoustic pulse lasted for 1.5 seconds, and then a pause of 1.5 seconds occurred until the next 1.5 second pulse. The amplitude of the initial 1.5 second pulse was 6 Vpp, and the amplitude of each pulse was increased by an amount of 3 Vpp for each subsequent 1.5 second pulse. During this process, the cells were imaged and quantified. For example, the number of attached cells and detached cells were imaged and calculated after each pulse. Using this approach, the detailed detachment or rupture force of several hundreds of cells were imaged and calculated for each pulse, and accordingly each measurement or calculation per pulse. After a 30-minute incubation of the cells in the acoustic device, the detachment process of the MCF-7 cells began by applying the gradually increasing amplitude 1.5 second pulses and imaging and quantifying the cells and calculating the corresponding rupture or detachment force corresponding to the amplitude. As illustrated in FIGS. 11A, 11B, 11C and 11D, the cells were attached to the substrate at the beginning, and as the amplitude of the pulse signals increased, the cells gradually detached from the substrate. After the amplitude reached 51 Vpp, and the streaming fluid applied a force of about 12 nN, about most or all of the cells had detached from the substrate. The experiment was repeated five times, and the resulting rupture force distribution of MCF-7 cells under different culture times were plotted, as shown in FIG. 12, which shows a direct correlation between rupture force and the time the cells were cultured. That is, as the culture time increased, so did the force required to discharge the cells from the substrate.

Figure 13:
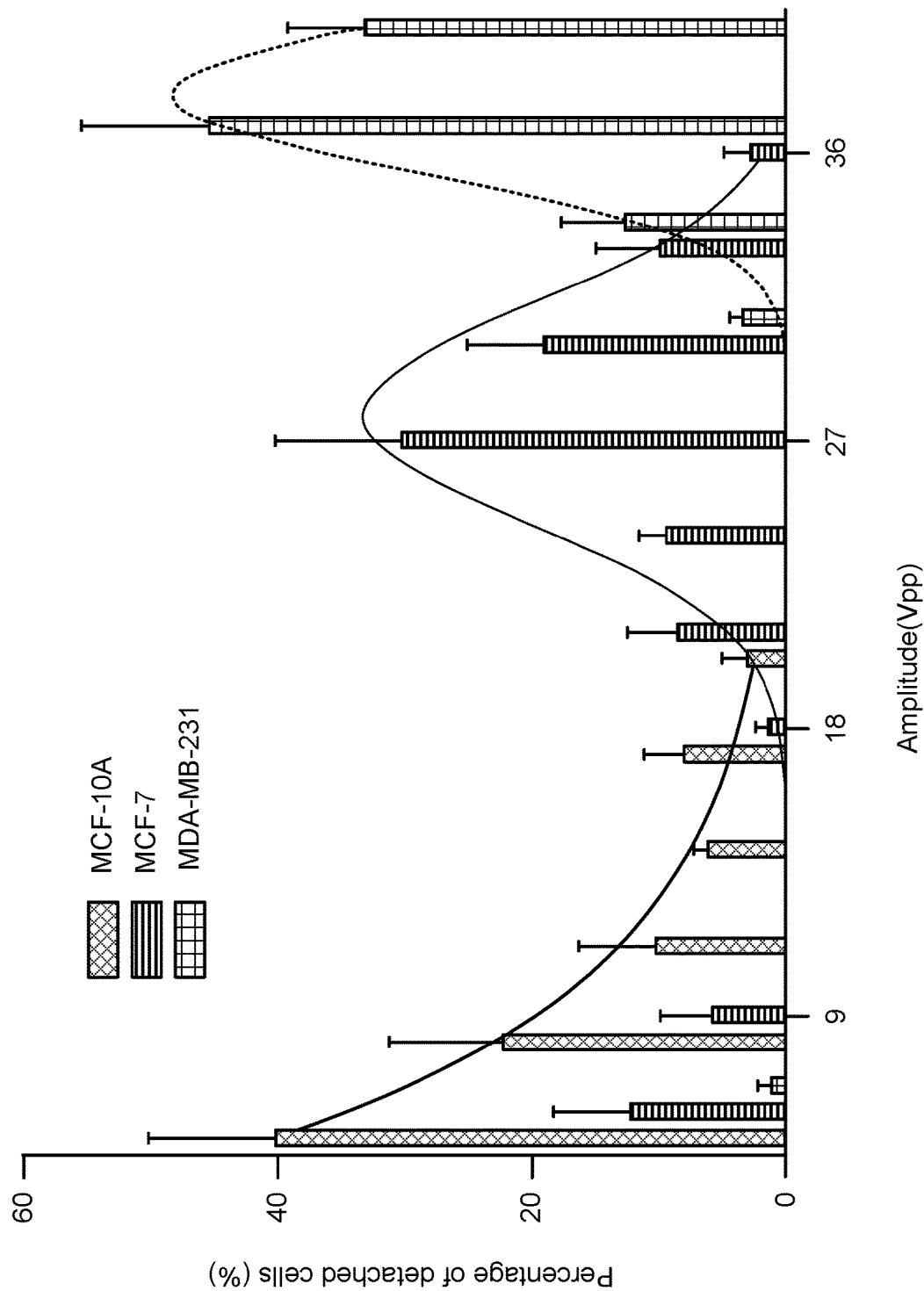
FIG. 13 illustrates a graph of the correlation between the percentage of detached cells and the signal amplitude for three different types of cancer cells.

Characterization of Metastatic Potential. The dynamic adhesion force of three breast cancer lines of cells to fibronectin using our acoustic streaming detachment device to mimic the dynamic adhesion force of CTCs to endothelial ECM in the tumor metastasis process. The three breast cancer lines included MCF-10A, MCF-7, and MDA-MB-231. MCF-10A is a non-tumorigenic breast epithelial cell line; MCF-7 cells are considered a poorly aggressive and noninvasive cell line, normally considered to have low metastatic potential; and MDA-MB-231 cells are regarded as a highly aggressive breast cancer cell line. These three breast cancer lines cells were cultured or incubated for 15 minutes the acoustic device 102, namely in the open chambers. Using the acoustic device 102 and method(s) of the present disclosure, rupture forces were measured, and rupture force maps were created. Referring to FIG. 13, the distribution of the detachment of the three different breast cancer cells to acoustic input amplitude was plotted. This figure illustrates that these three human breast cancer cells showed varied distribution patterns. Specifically, the MDA-MB-231 cells, which are the highly aggressive breast cancer cell line, adhered most strongly to the fibronectin-coated substrate, thereby demonstrating that this cell line has the greatest metastatic potential amongst the three lines. In comparison, the MCF-10A cell line, which is the nontumorigenic breast epithelial cell line, has the least metastatic potential, because the data shows that these cells can be detached with the lowest acoustic amplitude input. And the adhesion analysis showed that MCF-7 cells, which is viewed as having low metastatic potential, was between the MCF-10A and MDA-MB-231 cell lines.

In summary, digital acoustic device of the present disclosure can be used to determine the interaction between cells and ECM using localized acoustic streaming. The acoustic design used to profile the cell-matrix adhesion has great potential in a wide spectrum of biomedical applications. By digitally tuning of the input amplitude, the acoustic streaming force can be accurately adjusted and set to create very low forces, such as in the range of hundreds of piconewtons (pN) to tens of nanonewtons (nN). The present disclosure demonstrates that the acoustic device and the associated detachment technique can characterize the adhesion dynamics and kinetics of cells, such as cancer cells, to fibronectin. And because fibronectin mimics cells and/or cell matrices, the acoustic device and the corresponding method has broad application in determining the force(s) required to detach cells from other types of cells and/or cell matrices. Moreover, the acoustic device is an affordable device that is able to analyze hundreds of cells in parallel, while maintaining high precision. Moreover, the user-friendly feature of the digitally controlled device could be used to develop cancer diagnostic tools and implantable devices as well as to study fundamental biology.

Various modifications and additions can be made to the embodiments disclosed herein without departing from the scope of the disclosure. For example, while the embodiments described above refer to particular features, the scope of this disclosure also includes embodiments having different combinations of features and embodiments that do not include all of the described features. Thus, the scope of the present disclosure is intended to embrace all such alternatives, modifications, and variations as fall within the scope of the claims, together with all equivalents.

All publications, patents and patent applications referenced herein are hereby incorporated by reference in their entirety for all purposes as if each such publication, patent or patent application had been individually indicated to be incorporated by reference. Specifically, the following publication, including its supporting information, is incorporated by reference in its entirety: Profiling Cell-Matrix Adhesion Using Digitalized Acoustic Streaming, Hongwei Cai, Zheng Ao, Zhuhao Wu, Asael Nunez, Lei Jiang, Richard L. Carpenter, Kenneth P. Nephew, and Feng Guo, Analytical Chemistry 2020 92(2), 2283-2290.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for determining a cell binding force, the system comprising:
    an acoustic device comprising:
        a substrate;
        a plurality of open chambers disposed on the substrate, each of the plurality of open chambers having an area defined by at least one wall extending from the substrate, wherein the plurality of open chambers are configured to retain a suspension fluid comprising a plurality of cell matrices, each having a plurality of attached cells;
        one or more acoustic generators, including an interdigital transducer with a plurality of electrodes disposed in each of the plurality of open chambers between the at least one wall and a center of the open chamber, wherein the one or more acoustic generators are configured to create acoustic waves within the open chamber to produce a stream of the suspension liquid contained within the open chamber;
        a camera configured to image the plurality of cell matrices in the plurality of open chambers;
        a signal generator electrically coupled to the one or more acoustic generators, wherein the signal generator produces a signal having an amplitude;
        a controller comprising one or more processors and non-transitory computer readable medium storing instructions for execution by the one or more processors, wherein execution of the instructions by the one or more processors cause the one or more processors to:
    increase the amplitude of the signal;
    image the plurality of cell matrices as the amplitude of the signal is increased to identify an amplitude of the signal when one or more of the attached cells detach from one of the plurality of cell matrices;
    determine an estimated velocity of the stream of the suspension liquid based on the amplitude of the signal; and calculate a force at which one or more of the attached cells detach from one of the plurality of cell matrices using the estimated velocity.

2. The system of claim 1, wherein the interdigital transducer is a focused interdigital transducer.

3. The system of claim 2, wherein the plurality of electrodes of the focused interdigital transducer form an interlocking comb-shaped array.

4. The system of claim 1, wherein the plurality of electrodes have a focusing angle of between about thirty degrees and seventy-five degrees.

5. The system of claim 4, wherein the plurality of electrodes have a focusing angle of between about forty degrees and seventy degrees.

6. The system of claim 5, wherein the plurality of electrodes have a focusing angle of between about forty five degrees and sixty five degrees.

7. A system for determining a cell binding force, the system comprising:
 an acoustic device comprising:
  a substrate;
  a plurality of open chambers disposed on the substrate, wherein each the plurality of open chambers includes at least one wall extending from the substrate and configured to retain a suspension fluid comprising two or more cells bound to one another;
  one or more acoustic generators, including an interdigital transducer with a plurality of electrodes disposed adjacent each of the plurality of open chambers between the at least one wall and a center of the open chamber, wherein the one or more acoustic generators are configured to create an acoustic stream of the suspension fluid within the open chamber;
 a camera configured to image the two or more cells in each of the plurality of open chambers in parallel;
 a signal generator electrically coupled to the one or more acoustic generators, wherein the signal generator produces a signal having an amplitude;
 a controller comprising one or more processors and non-transitory computer readable medium storing instructions for execution by the one or more processors, wherein execution of the instructions by the one or more processors cause the one or more processors to:
  digitally increase the amplitude of the signal to the one or more acoustic generators;
  image the two or more cells in each of the plurality of open chambers as the amplitude of the signal is increased to identify an amplitude of the signal for each of the plurality of open chambers when one or more of the two or more cells detach from another of the two or more cells;
  determine an estimated velocity of the acoustic stream of the suspension liquid in each of the plurality of open chambers based on the amplitude of the signal; and
  calculate a force at which the one or more cells of the two or more cells detaches from the other of the two or more cells in each of the plurality of open chambers using the estimated velocity.

8. The system of claim 1, wherein the one or more acoustic generators produces standing surface acoustic waves.

* * * * *